United States Patent [19]
Santus et al.

[11] Patent Number: 5,571,533
[45] Date of Patent: Nov. 5, 1996

[54] CONTROLLED-RELEASE MUCOADHESIVE PHARMACEUTICAL COMPOSITION FOR THE ORAL ADMINISTRATION OF FUROSEMIDE

[75] Inventors: Giancarlo Santus, Milan; Giuseppe Bottoni, Bergamo; Caterina Lazzarini, Milan, all of Italy

[73] Assignee: Recordati, S.A., Chemical and Pharmaceutical Company, Chiasso, Switzerland

[21] Appl. No.: 240,033

[22] Filed: May 9, 1994

Related U.S. Application Data

[63] Continuation-in-part of Ser. No. 174,191, Dec. 27, 1993, Pat. No. 5,472,704, which is a continuation of Ser. No. 832,229, Feb. 7, 1992, abandoned.

[30] Foreign Application Priority Data

May 21, 1993 [IT] Italy .................... MI93A1049

[51] Int. Cl.[6] .................................. A61K 9/26
[52] U.S. Cl. .............................. 424/469; 424/498
[58] Field of Search .................. 424/78.04, 484, 424/469, 498

[56] References Cited

U.S. PATENT DOCUMENTS

| | | | |
|---|---|---|---|
| 3,288,824 | 11/1966 | Mahler et al. | 554/168 |
| 3,699,963 | 10/1972 | Zaffaroni | 424/435 |
| 4,226,848 | 10/1980 | Nagai et al. | 514/772.1 |
| 4,713,243 | 12/1987 | Schiraldi et al. | 424/676 |
| 4,940,587 | 7/1990 | Jenkins et al. | 424/480 |
| 5,028,432 | 7/1991 | Chopra et al. | 424/484 |
| 5,310,558 | 5/1994 | Pozzi et al. | 424/476 |
| 5,403,847 | 4/1995 | Gluchowski et al. | 514/318 |

FOREIGN PATENT DOCUMENTS

| | | |
|---|---|---|
| 0205282 | 12/1986 | European Pat. Off. . |
| 0239361 | 9/1987 | European Pat. Off. . |
| 0330532 | 8/1989 | European Pat. Off. . |
| 0387782 | 9/1990 | European Pat. Off. . |
| 0452268 | 10/1991 | European Pat. Off. . |
| 0516141A1 | 2/1992 | European Pat. Off. . |
| 2497098 | 2/1982 | France . |
| 85/02092 | 5/1985 | WIPO . |
| WO-A-8910117 | 11/1989 | WIPO . |

OTHER PUBLICATIONS

An In-Vitro Investigation of Mucosa-Adhesive Materials for Use in Controlled Drug Delivery, Smart et al., *J. Pharm. Pharmacol.* 1984, 36: 295–99.

In Vitro Method to Evaluate Bioadhesion of Microparticles, Sala et al., *Proceeed. Intem. Symp. Control. Rel. Bioact. Mater.*, 16 (1989), Controlled Release Society, Inc., pp. 420–421.

The Gastric Emptying of Hard Gelatin Capsules, Hunter et al., *International Journal of Pharmaceutics*, 17 (1983) 59–64.

Experimental Methods for Determination of Bioadhesive Bond Strength of Polymers with Mucus, Peppas et al., *S.T.P. Pharma* 5(3) 187–191, 1989.

R. Khosla et al., *J. Pharm. Pharmacol*, 39:47–49, 1987.

Patent Abstracts of Japan, vol. 12, No. 47, Feb. 12, 1988—Abstract of Japanese Application No. JP62195336.

Verhoeven, J. et al., A controlled-release matrix table of furosemide: design, in vitro evaluation, pharmacological and pharmacodynamic evaluation, International Journal of Pharmaceutics, 45 (1988) 65–77.

(List continued on next page.)

*Primary Examiner*—Peter F. Kulkosky
*Attorney, Agent, or Firm*—Darby & Darby, P.C.

[57] ABSTRACT

Disclosed are controlled-release mucoadhesive pharmaceutical compositions for the oral administration of furosemide. This composition comprises a multiplicity of microgranules of lipophilic material which are coated with a mucoadhesive coating. This invention reduced or eliminates the diuresis peak and reduces inter-subject response variability which normally accompany conventional treatment with this drug.

27 Claims, 4 Drawing Sheets

OTHER PUBLICATIONS

Ebihara A. et al, *Pharmacodynamic and Pharmacokinetic Study of a Slow–release Formulation of Furosemide in Man,* Drug Res. 33 (I), Nr. 1, pp. 163–166 (1983).

Deutsche Apotheker Zeitung, vol. 130, No. 15, Apr. 12, 1990, pp. 791–801 (in German).

List, P. H. et al., Hagers Handbuch Der Pharmazeutischen Praxis, 1971, pp. 312–315 (in German).

Lehr et al., *J. of Controlled Release* 13: 1, 51–62, Jul., 1990.

Farmacopea Officiale Della Repubblica Italiana 9th Ed., Suppl. 1991, pp. 405–407.

CONTROLLED-RELEASE MUCOADHESIVE PHARMACEUTICAL COMPOSITION FOR THE ORAL ADMINISTRATION OF FUROSEMIDE

RELATED APPLICATIONS

This application is a continuation-in-part of U.S. patent application Ser. No. 08/174,191 filed Dec. 27 1993, now U.S. Pat. No. 5,472,704 which is a continuation of Ser. No. 07/832,229 filed Feb. 7, 1992, now abandoned.

FIELD OF THE INVENTION

This invention relates to a controlled-release mucoadhesive pharmaceutical composition for the oral administration of furosemide.

BACKGROUND OF THE INVENTION

Furosemide (4-chloro-2-furfurylamino-5-sulphamoyl benzoic acid) is a drug with a diuretic action which acts at the renal level on the ascending limb of the loop of Henle. In addition to possessing a strong, rapid and short diuretic action, furosemide has a hemodynamic effect on the heart. Furosemide-induced diuresis begins within 20 minutes from oral dosing and stops in 4–5 hours.

This drug is used in the treatment of oedema of pulmonary, cardiac or hepatic origin as well as in the treatment of hypertension and in the chronic treatment of cardiac infarction.

However, use of furosemide in the foregoing treatments is often accompanied by adverse effects, the most important of which are the presence of a high diuresis peak and a marked drug absorption variability.

The diuresis peak causes most of the urinary excretion induced by furosemide to occur in the initial hours following administration, which causes weakness and fatigue symptoms particularly in elderly patients.

Absorption variability can be seen within the same patient after repeated doses as well as in different patients.

These adverse effects are traced to the fact that furosemide is absorbed and metabolized mostly at the gastric level and, to a lesser extent, at the level of the upper section of the intestine (Verhoeven J et al., Int. J. Pharm. 45, 65 (1988)).

The formulations for the administration of furosemide presently on the market include fast-release tablets containing 20 to 500 mg of active ingredient, and injectable formulations containing 10 mg/ml. Controlled-release formulations are also known.

Generally, the fast-release formulations are used in the acute treatment of oedema, whereas controlled-release formulations are preferred in the chronic treatment of hypertension and cardiac infarction.

The controlled-release formulations were intended to reduce the diuresis peak while maintaining the quantity of urine excreted within 24 hours equal to that excreted with fast-release formulations. A controlled release formulation containing furosemide is disclosed in Ebihara et al. (*Drug Res.* 33, 163 (1983)); this formulation, however, does not have bioadhesive properties. In any case, the use of prior art controlled release formulations increases the above erratic absorption problem.

Patent application EP 277,925 describes an enteric-coated formulation with variable release, i.e. a formulation that has controlled release properties at pH 5–6, and immediate release properties at pH 7.4. This formulation attempts to avoid the diuresis peak by reducing release in the site of greater absorption and facilitating total drug release towards the end of the absorption window. However, this type of formulation eliminates gastric absorption, which, in the case of furosemide, results in a low drug bioavailability with a consequent reduced drug efficacy (Verhoeven J. et al., ibidem).

Patent EP 239,361 describes enteric-coated micro capsules containing furosemide, coated with an intermediate ethylcellulose film and an outer cellulose acetate phthalate film. However, considering the relatively slow release of furosemide from the microcapsules at pH 7.5 and considering that the transit of a solid dosage form through the upper section of the gastrointestinal tract takes about 6 hours (Harris D. et al., J. of Contr. Rel. 12, 45 (1990)), the release of this formulation is also likely to occur mostly outside the furosemide absorption window.

In addition to the above controlled-release formulations, a hydrophilic matrix containing furosemide is also known. This type of formulation releases about 94% of the drug content in 8 hours at pH 6.8 (Verhoeven J. et al., ibidem).

While more effective than a fast-release formulation (it achieves the same diuretic effects with a lower quantity of furosemide), the hydrophilic matrix formulation is incapable of avoiding a diuresis peak which appears to be comparable with that obtained with a fast-release dose.

As can be seen from the above, none of the solutions known to date can simultaneously solve the problems of erratic absorption and diuresis peak which accompany furosemide administration.

The use of bioadhesive pharmaceutical compositions to extend the residence in the host of controlled-release formulations is generally known. In particular, mucoadhesive materials have the property of adhering to mucous membranes for extended periods of time. In the gastrointestinal tract the residence of mucoadhesive materials extends at most to about 24 hours due to the daily replacement of the mucous membrane.

For instance, international patent application WO 85/02092 describes a pharmaceutical composition for the treatment of skin and mucous membranes which has bioadhesive properties. The bioadhesive agents used are fibrous, crosslinked and water-swelling (but not water-soluble) carboxy-functional polymers. The composition takes various dosage forms including an intimate mixture of the active ingredient with bioadhesive polymers, capsules, films or laminates.

Another example is disclosed in European patent EP 205,282 which describes a controlled-release pharmaceutical composition containing cellulose, capable of adhering to mucous membranes. This composition, in a solid dosage form and suitable for oral or nasal administration, consists of granules coated with mucoadhesive cellulose. The granules contain the active ingredient, a long-chain aliphatic alcohol and a water-soluble hydrous hydroxyalkylcellulose used both as a granule ingredient and as an extragranular ingredient.

A third example is disclosed in the U.S. Pat. No. 4,226,848, which describes an administration method employing a bioadhesive pharmaceutical composition. The composition contains a bioadhesive polymer matrix with the active ingredient dispersed within it which adheres to the oral or nasal cavities. In this case the bioadhesive matrix is made up of both a cellulose ether and a homopolymer or copolymer of acrylic acid.

It should be noted that none of the above-mentioned patents/applications discloses any formulation for the controlled release of furosemide.

Copending commonly assigned U.S. patent application Ser. No. 07/832,229 now abandoned discloses controlled release compositions with mucoadhesive properties comprising microunits with a controlled-release (non mucoadhesive) core containing the active ingredient and coated with a mucoadhesive. The mucoadhesive coating is selected to confer to the composition predetermined mucoadhesive characteristics and the core excipients are selected to produce a predetermined release profile for the active ingredient. This arrangement permits to control bioadhesive characteristics separately from release control characteristics, i.e. optimization of the former does not interfere with optimization of the latter.

Furosemide is mentioned as one of the active ingredients which can be administered by compositions of the prior copending application. However, this application does not take into consideration the additional technical problems of lowering diuresis peak and avoiding the erratic absorption which is typical of the dosage forms for this drug.

It has now surprisingly been found that, if the microunits for the controlled release of furosemide which are coated with mucoadhesive polymers are formulated as microgranules, so that the excipients used for granulation have an HLB (Hydrophilic Lipophilic Balance) lower than 8, a pharmaceutical composition for the controlled release of furosemide is obtained which is particularly effective in correcting erratic drug absorption and, therefore, substantially reducing therapeutic response variability in a host treated with furosemide. The full range of HLB values is from 1 to 50.

At the same time, this composition also limits the diuresis peak which normally follows drug administration, so that a formulation is obtained which is particularly suitable to be used in chronic administration of furosemide.

OBJECTS OF THE INVENTION

An object of the present invention is, therefore, to provide a pharmaceutical composition containing furosemide ingredient dispersion on the mucous membrane surfaces so as to ensure satisfactory bioavailability, consistent absorption and a low diuresis peak.

SUMMARY OF THE INVENTION

Figure 1:
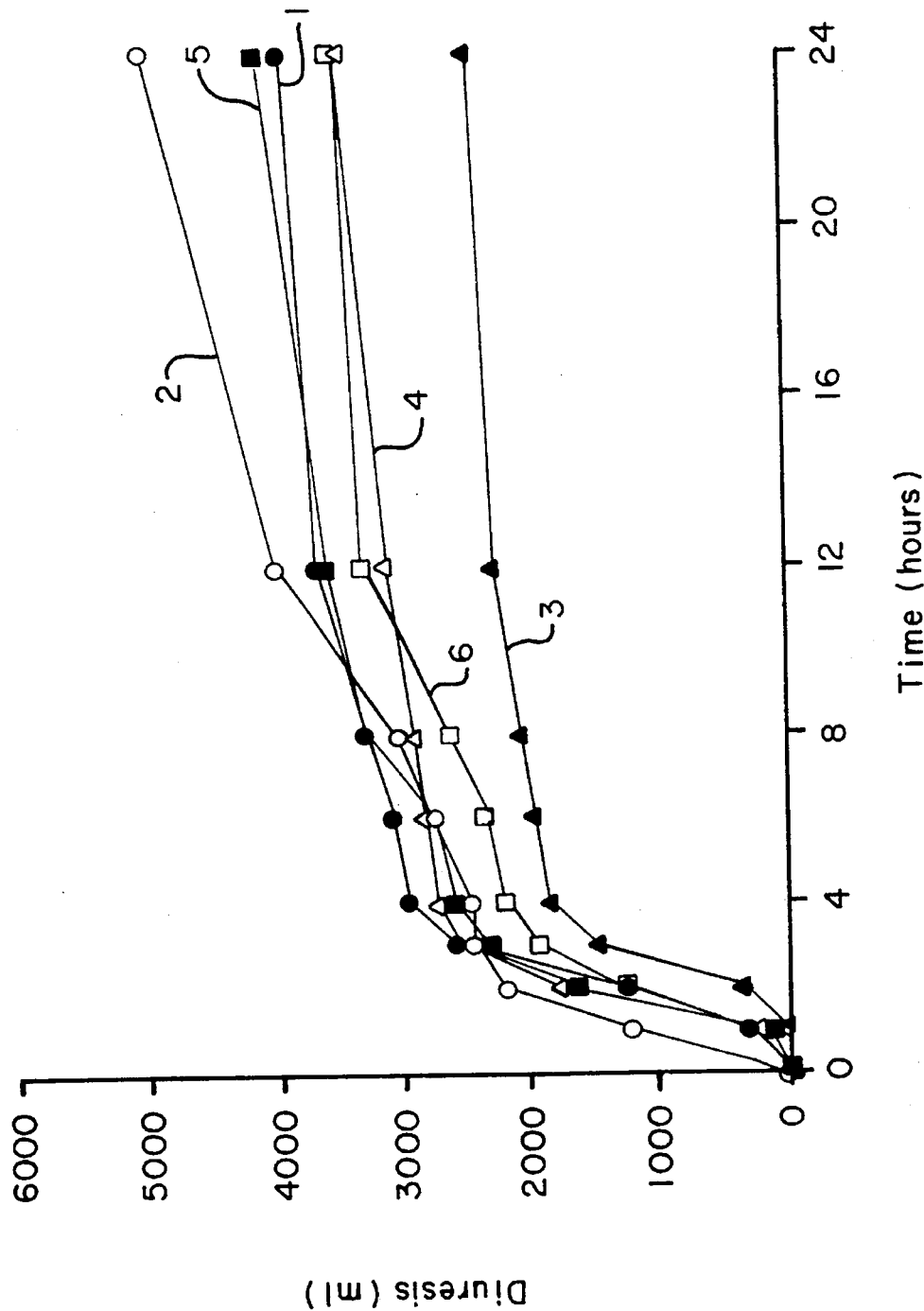
FIG. 1 shows the cumulative diuresis profiles for 6 volunteers after administration of the fast-release formulation (O) (PRIOR ART).

Generally, the present invention relates to a pharmaceutical composition which contains a multiplicity of microgranules capable of controlling the release of furosemide which comprise a mixture of the active ingredient and appropriate release-control excipients. The excipients which control the release of the active ingredient (granulation excipients, also referred to as "melted mass") are of an overall hydrophobic non-mucoadhesive nature, and have an HLB lower than 8, and, preferably, higher than or equal to 2.

The microgranules are detached from one another and are coated with at least one mucoadhesive material capable of ensuring adhesion of the microgranules to the gastrointestinal tract.

The composition also contains extragranular excipients capable of ensuring, after administration of the composition, a uniform dispersion of the mucoadhesive granules on the surface of the mucous membrane section responsible for furosemide absorption.

The administration of this formulation yields a low variability urinary excretion profile in the subjects treated. In particular, diuresis after 24 hours was comparable with that normally measured following administration of an equal furosemide quantity contained in a fast-release formulation. A nearly complete removal of the diuresis peak was also evident.

DETAILED DESCRIPTION OF THE INVENTION

Furosemide, in a quantity equal to 60–70% by weight of the mixture, is first mixed with hydrophobic ingredients. This mixture is then granulated by the addition of a melted mass of both hydrophobic and hydrophilic ingredients so as to confer an overall HLB to the melted mass lower than 8. The intended control release profile for the composition is to provide a slow and complete drug release over about 24 hours. Microgranules of sizes ranging from 125 to 500 microns and capable of providing a slow and complete release of furosemide over 24 hours are preferred.

It is important to stress that the in vitro dissolution tests showed that no granulating excipients with an HLB higher than 8 can ensure this type of release for furosemide. From a practical point of view, it is also important that the melting characteristics of the granulating mass be such as to permit the process to be carried out with normal equipment in the usual operating conditions. The melting point of the granulating mass should not be very high (100° C. at maximum) and the solidification range has to be wide enough (35°–100° C. approximately) to keep the granulating mass always melted and effective even if we use a granulator not equipped with a heating jacket (as is usual for most laboratory granulators.)

The excipients which permit to obtain a mixture having a suitable melting point and HLB include without limitation saturated or polyglycolyzed glycerides e.g. mixtures of glycerol monoesters, diesters or triesters, as well as mixtures of polyethyleneglycol monoesters or diesters with fatty acids such as caprylic acid (C8), capric acid (C10), lauric acid (C12), myristic acid (C14), palmitic acid (C18), or stearic acid (C18).

The characteristics and identification tests for saturated glycerides are described in the Italian (II Supplemento 1991, Gliceridi Polyglycosati Saturi, pp. 405–407) and French (Jan. 1990, Glycerides Polyglycolyses Satures pp. 1–4) Pharmacopoeias.

Examples of the values that characterize four of these excipients are set forth in Table A. As the HLB values are additive, fatty excipients having an HLB value higher than 8 may be mixed with fatty excipients having an HLB value lower than 8 (e.g. excipient D may be mixed with excipient A) in order to obtain a mixture of fatty excipients which falls into the preferred ranges. For the purpose of the present application, only the melting point and HLB values are relevant.

TABLE A

|   | M.P. (°C.) | HLB | ACIDIC | SAPONIFICATION | HYDROXYL | IODINE |
|---|---|---|---|---|---|---|
| A | 46.5–51.5 | 2 | <2 | 120–125 | 24–25 | <2 |
| B | 59.0–70.0 | 5 | <5 | 70–90 | <60 | <10 |
| C | 47.0–52.0 | 7 | <2 | 125–140 | 65–85 | <2 |
| D | 46.0–51.0 | 9 | <2 | 105–125 | 60–80 | <2 |

The above values are defined in USP XXII (1990), pp 1535–1536.

These excipients can be easily obtained from vegetable oils (e.g. coconut or palm oil) by means of alcoholysis, or, conversely, by esterification of the above mentioned fatty acids according to well known methods (March, Advanced Organic Chemistry 3rd Ed., pp 348–352, 1985, Wiley, New York; or U.S. Pat. No. 3,288,824).

Some of these saturated polyglycolyzed glycerides are marketed under the name of GELUCIRE™ by Gattefosse S. A. (Saint Priest, France) and are sold in fractions identified by means of a number that indicates both the corresponding melting point and the HLB (Hydrophilic Lipophilic Balance) value. For instance, GELUCIRE™ 50/02 indicates a fraction of saturated polyglycolyzed glycerides having a melting point of 50° C. and an HLB value equal to 2. The characteristics corresponding to Gelucire 50/02 are described in Table I under A. In the same Table, B denotes Gelucire 62/05; C denotes Gelucire 46/07; and D denotes Gelucire 48/09. An HLB value lower than 8 can be achieved using as a granulating mixture either a single GELUCIRE™ or a mixture of various GELUCIRE™ products with the same or different HLBs. In the latter case, the granulation excipients should be in such a ratio (or ratios) as to provide an overall HLB within the desired limit. The hydrogenated castor oil is not included in the HLB calculation, as it is a substance having full hydrophobic characteristics.

Further examples of commercially available excipients that are suitable for use in the present invention (alone or in various combinations) and that are not included under the GELUCIRE trademark are: glyceryl tristearate (HLB 1; m.p. 55° C.; glyceryl monostearate (HLB 3.8, m.p. 56°–58° C.); glyceryl monopalmitate stearate (HLB 4.5, m.p. 53°–57° C.); glyceryl monomyristate (HLB 6.0, m.p. 56° C.); polyethyleneglycol monostearate (HLB 16.5, m.p. 45°–49° C.); and polyethyleneglycol palmitatestearate (HLB 11; m.p. 30°–35° C.). These are available, e.g., from Sigma Chemical Co., St. Louis Mo., or ICN, Costa Mesa Calif.

The calculation methods for selecting the mixture of ingredients and the ratios required to obtain the desired HLB can be found in Remington's Pharmaceutical Sciences, 18th Ed., pages 304–306 (1990), Mack Publishing Company—Easton, Pa.

For instance, appropriate mixtures of GELUCIRE™ 50/02, 64/02 or 37/02 with GELUCIRE™ 35/10, 50/13 or 42/12 can be used as an alternative to GELUCIRE™ 62/05.

Even though there are many and varied usable mixtures, the best results, from a furosemide-release point of view, were found to be obtained using GELUCIRE™ 62/05 or mixtures of GELUCIRE™ 50/02 with GELUCIRE™ 48/09. For mixtures of GELUCIRE 50/02 with GELUCIRE 48/09, examples of a ratio range are: 1.5:1 to 4:1.

The controlled-release granules so obtained are then coated with one or more mucoadhesive polymers which make the granules themselves capable of adhering to the gastrointestinal mucus. The final sizes of the coated granules are then selected so as not to exceed a geometrical diameter of about 600 microns.

A variety of polymers, which are already known in the literature as being mucoadhesive, can be used in order to coat the controlled-release microgranules, including for instance polyacrylic polymers, such as carbomer and its derivatives, or cellulose derivatives, such as hydroxypropylmethylcellulose, hydroxyethylcellulose, hydroxypropylcellulose and sodium carboxymethylcellulose. Combinations of two or more mucoadhesive polymers can also be used.

Carbomer and hydroxypropylmethylcellulose proved to be particularly useful for the purpose of the invention.

Although the weight ratio between the controlled-release granules and the mucoadhesive polymer may range from 5:1 to 0.1:1, the best results for the purposes of the present invention are obtained with ratios from 2.5:1 to 0.5:1.

Though even one mucoadhesive polymer only can be sufficient to coat the microunits, it was found that a mixture of mucoadhesive polymers with different characteristics yields better results. In particular, the characteristics of the mucoadhesive coating are more persistent when this coating is made up of mixtures of acrylic polymers and cellulose derivatives such as mixtures of carbomer and hydroxypropylmethylcellulose. Suitable references for important characteristics and the most effective mixtures can be found in co-pending U.S. patent application Ser. No. 07/832,229, page 11, lines 7–27, which is hereby incorporated by reference in its entirety.

The ratios between the ingredient with more clearly mucoadhesive characteristics (e.g., an acrylic polymer) and the ingredient which acts as a binder (e.g., a cellulose derivative) may range from 0.2:1 to 20:1. In the formulation which is an object of the invention optimum results are obtained using ratios between 0.5:1 and 5:1.

A quantity of lubricant capable of improving the compression characteristics of the mixture, but also incapable of changing the release profile or reducing mucoadhesion characteristics, is optionally added to the mixture containing the mucoadhesive film and the controlled-release granules. A typical but nonlimiting amount of lubricant is about 1% w/w of the whole composition.

These lubricants can be selected from those commonly used, including, for instance, stearic acid and related salts (magnesium stearate, zinc stearate, calcium stearate), leucine, talc, glyceryl fumarate, hydrogenated vegetable oils, polyethylene glycols and other compounds with a similar behavior.

Coating of the cores with mucoadhesive materials is carried out by a coating method based on the principle of dry granulation coating. The microgranules are intimately mixed with a mucoadhesive polymer, or with a mucoadhesive mixture of polymers, and with a lubricant, if any, and the whole is then subjected to compression. The compacted mass so obtained is next crumbled and the granules are sieved to obtain particles of the desired sizes (125–600 microns).

In this manner the individual microgranules can be coated with the necessary polymer quantity so as to obtain the desired mucoadhesive properties.

Also in the case of mixtures, even though the weight ratio between the controlled-release granules and the mucoadhesive polymer mixture may range 5:1 to 0.1:1, the best results are obtained with ratios from 2.5:1 to 0.25:1.

Subject to not adversely affecting mucoadhesive properties, as stated above, the quantity of lubricant is not crucial for coating and can be established using no more than routine experimentation on the basis of the operating conditions and equipment used.

To be conveniently administered by the oral route, the composition which is an object of the invention is formulated into appropriate dosage forms, which are preferably hard gelatine capsules containing the microgranules.

If hydration and swelling of the microgranule coating begins before the microgranules are completely out of the capsule, the microgranules tend to adhere to each other and lose much of their ability to adhere to the mucus which lines the intestinal mucous membrane. In fact, in that event, the microgranules tend to behave as a normal single-dose dosage form and the advantage provided by the large contact surface between the mucus and the dosage form, which is the main reason for selecting the described microgranulation technique, may be curtailed or even lost.

To avoid this drawback, the mucoadhesive microgranules are mixed with a hydrophobic substance whose function is to coat the particles and delay hydration of their coatings, and with a disintegrating substance whose purpose is to speed up exit of the microgranules from the capsule, thus ensuring dispersion of the mucoadhesive microunits on the surface of the gastrointestinal mucous membrane.

Substances suitable to delay hydration are, for instance, magnesium stearate, calcium stearate, talc or other known substances with similar water scavenging properties.

Disintegrating substances are, for instance, crosslinked polyvinylpyrrolidone, carboxymethylstarch, croscarmellose sodium, starch or other known substances with similar properties.

The hydrophobic ingredient content ranges between 1% and 10% of the total weight of the mixture ingredients placed in the capsule, whereas that of the disintegrating component ranges between 2% and 20%.

The capsules, appropriately packed with the mucoadhesive granule mixture and the extragranular excipients, can preferably ensure administration of a 40-mg dose of furosemide. However, the present invention is not limited to compositions containing 40 mg furosemide. Different effective furosemide amounts such as those known in the art and described above for oral formulations can be used.

The above mucoadhesive formulation, while inducing a 24-hour total urinary excretion equal to that which can be obtained with the administration of an equal amount of fast-release furosemide, shows no diuresis-peak drawback, with a significantly increased patient compliance and a reduction in the side effects which are typical of fast-release formulations. The patient compliance increases because of fewer and less severe side effects and because of diuresis-peak reduction or elimination.

Furthermore, doses being equal, the variability in the inter-subject responses to treatment with the mucoadhesive formulation is considerably reduced compared to the variability which observed after treatment with fast-release formulations.

Some examples are provided below, which are intended to describe in detail how the object of the present invention can be achieved and the advantages provided by its application. These examples are in no way intended as a limitation of the invention in particular as far as the materials and techniques used are concerned.

The examples were obtained using in particular the following equipment: TURBULA mixer (Willi A. Bachofen AG, Basel, Switzerland); TONAZZI mixer (Tonazzi Vittorio e C. S.r.l., Milan, Italy); DIOSNA granulator (Dierks & Söhne, Osnabrück, Germany); ERWEKA granulator (Erweka GmbH, Heusenstamm, Germany); RONCHI rotary tableting machine (Officine Meccaniche Fratelli Ronchi, Cinisello Balsamo, Italy).

EXAMPLE 1

Controlled-Release Granules

Five different controlled-release granulates were prepared with the percent compositions described in Table 1:

TABLE 1

| Components | | Composition % | | | | | |
|---|---|---|---|---|---|---|---|
| | | A | B | C | D | E | F |
| Mixing Phase | FUROSEMIDE | 22.2 | 44.5 | 44.5 | 44.5 | 44.5 | 50.0 |
| | HYDR.CASTOR-OIL | 11.1 | 22.2 | 22.2 | 22.2 | 22.2 | 24.8 |
| | Ca PHOSPHATE | 22.2 | — | — | — | — | — |
| Granulat. Phase | HYDR.CASTOR-OIL | 11.1 | 11.1 | 11.1 | 11.1 | 11.1 | 8.4 |
| | GELUCIRE ™ 50/02 | 22.2 | 22.2 | — | 17.8 | — | 10.0 |
| | GELUCIRE ™ 48/09 | — | — | 22.2 | 4.4 | — | 6.8 |
| | GELUCIRE ™ 64/05 | — | — | — | — | 22.2 | — |

GELUCIRE ™ : polyoxyethylene and polyglycolyzed glycerides (Gattefosse S.A., Saint Priest - France)

Granulate Preparation

If the formulation is prepared in a mixer/granulator, the mixture ingredients are mixed in the mixer for 5 minutes. The mixture obtained is then further mixed in the same apparatus with the ingredients of the granulating phase pre-melted at a temperature of approximately 80° C. and granulation is continued for another 10 minutes. The resulting granules are crumbled to obtain particles with sizes ranging between 125 and 500 microns.

If a fast granulator is used, the mixing/granulating procedure is identical, but the final granulation time must be reduced from 10 to 1 minute.

Release Control

The six preparations A–F obtained as described in Example 1 were characterized by their respective release profiles.

Table 2 shows the results of the dissolution tests performed in accordance with the specifications for Apparatus II in USP XXII Ed., at the following conditions: dissolution medium: phosphate buffer pH 5.8, 900 ml; temperature: 37° C.; stirring: 50 rpm; detector: UV (absorption) 274 nm.

Taking into consideration the dissolution profiles of formulations A and B, which contained GELUCIRE™ with HLB=2, a slow but incomplete drug release could be seen over 24 hours. However, the dissolution curve of formulation C, which contains GELUCIRE™ with an HLB=9, showed too rapid a release to be useful in a furosemide-containing formulation. This demonstrates that the HLB levels of the granulating agents exercise a determinant effect on the furosemide release rate from the formulation. In fact, formulations D, E and F, which also used GELUCIRE™ with intermediate HLBs compared to those used in formulations A, B and C, showed a drug release which was both slow and complete over a period of 24 hours.

TABLE 2

| Time    | % Furosemide Released |       |       |       |       |       |
|---------|-------|-------|-------|-------|-------|-------|
| (hours) | A     | B     | C     | D     | E     | F     |
| 1       | 30.9  | 25.1  | 50.1  | 30.9  | 32.1  | 31.2  |
| 2       | 40.8  | 31.1  | 68.1  | 48.4  | 44.8  | 42.9  |
| 4       | 50.5  | 42.9  | 81.3  | 61.4  | 58.5  | 56.0  |
| 8       | 63.7  | 52.4  | 89.7  | 72.5  | 71.8  | 69.6  |
| 12      | <75.0 | <75.0 | >90.0 | >75.0 | >75.0 | >75.0 |
| 24      | <80.0 | <80.0 | —     | >90.0 | >90.0 | >90.0 |

The determinant influence of the HLB levels of the excipients used in the melted granulating mass, as far as the in vitro drug release control is concerned, is further confirmed by comparing the dissolutions of formulations A and B.

In these formulations the difference in composition was the presence or absence of a hydrophilic element such as calcium phosphate. As can be seen, drug release is substantially identical for the two formulations, which means that the hydrophilic element by itself did not influence the behavior of the formulation.

EXAMPLE 2

Mucoadhesive Granules for the Controlled Release of Furosemide

Controlled-release mucoadhesive granulates with the percent composition shown in Table 3 were prepared using some of the controlled-release (c.r.) cores described in Example 1:

TABLE 3

|         |             | G    | H  | I  | L  |
|---------|-------------|------|----|----|----|
|         |             | Composition % |  |  |  |
| C.R.    | GRANULATE A | 33.3 | 33 | —  | —  |
| Cores   | GRANULATE B | —    | —  | 33 | —  |
|         | GRANULATE D | —    | —  | —  | 33 |
| Coating | CARBOPOL 934| 33.3 | 33 | 33 | 33 |
|         | METHOCEL E4M| 33.4 | 33 | 33 | 33 |
|         | LEUCINE     | —    | 1  | 1  | 1  | where:
Carbopol 934: copolymer of acrylic acid (Goodrich Chemical);
Methocel E4M: hydroxypropylmethylcellulose with a 4000 cps viscosity in a 2% aqueous solution (Dow Chemical);

The controlled-release granulate was added to the mixture of the two polymers which made up the mucoadhesive coating. Where necessary, a lubricant (leucine) was then also added to the mixture obtained. The final mixture was compacted with a rotary tableting machine using a compression force of approximately 8 KiloNewtons (KN), obtaining a compacted mass with a diameter of 11.25 mm. The compacted mass was crumbled and sieved to obtain coated granules with a diameter ranging between 125 and 600 microns.

Release Control

The four preparations G–L were characterized by the respective release profiles of the furosemide contained. The dissolution tests were conducted in accordance with the conditions described in Example 1. The results are shown in Table 4.

TABLE 4

| Time    | % Furosemide Released |       |       |       |
|---------|-------|-------|-------|-------|
| (hours) | G     | H     | I     | L     |
| 1       | 31.3  | 34.3  | 28.6  | 31.0  |
| 2       | 40.7  | 43.6  | 37.3  | 47.9  |
| 4       | 50.3  | 52.3  | 44.6  | 59.9  |
| 8       | 60.7  | 61.5  | 56.0  | 71.3  |
| 12      | >75.0 | >75.0 | <75.0 | >75.0 |
| 24      | >80.0 | >80.0 | <80.0 | >90.0 |

Evaluation of Mucoadhesive Properties

An in-vitro evaluation of the mucoadhesive properties of the formulations which are an object of the invention was performed directly on the granules coated with a mucoadhesive mixture using the apparatus and method described by G. Sala et al., Proceed. Int. Symp. Contr. Rel. Bioact. Mat. 16, 420, (1989). This apparatus operates by measuring the water flow required to remove the granules from a strip of rabbit intestinal mucous membrane fled horizontally in an appropriate temperature-controlled chamber at 37° C. The tissue was first washed with preestablished volumes of water, with a peristaltic pump, an exact quantity by weight of granules was then placed on the tissue and allowed to stand for 2 minutes to ensure appropriate hydration of the granule mucoadhesive coating. At the end the granules were eluted with water pushed by a peristaltic pump for 10 minutes, the washed granules were pooled, and the active ingredient content was determined by U.V. titration in order to determine the exact percentage of particles removed. Various tests were performed using increasing eluting flows. The regression values were calculated and the water flow required to remove 50% of the particles from the mucous membrane surface within a preestablished time of 10 minutes ($F_{50}$) was measured.

The results are shown in Table 5 where the removed percentages for different water flows and the respective $F_{50}$ values are indicated. The mucoadhesion test was applied both to particles with a mucoadhesive coating (G, H, I, L) and to particles with no mucoadhesive coating (D, M), which were considered as a reference for the purpose of this test.

TABLE 5

| Flow (ml/min) | D | G | H | I | L | M |
|---|---|---|---|---|---|---|
| | | | % Microgranules Removed | | | |
| 7 | 98.0 | — | — | — | — | 98.0 |
| 15 | — | 7.1 | 6.6 | 10.5 | 3.0 | — |
| 19 | — | 12.2 | 11.1 | 13.7 | 12.0 | — |
| 23 | — | 20.9 | 16.1 | 20.3 | 14.3 | — |
| $F_{50}$ | — | 40.6 | 52.9 | 47.8 | 48.6 | — |

Formulations (D, G, H, I, L) were obtained as described in Examples 1 and 2, formulation (M) was made up of enteric-coated granules obtained from the content of hard gelatine capsules available commercially as Lasix-Long™.

The data shown in Table 4 indicate that the application of a mucoadhesive film does not change the release profile of furosemide from the controlled-release granules, whereas it is apparent from those in Table 5 that the presence of a mucoadhesive coating makes the percentage of granules removed from the mucous membrane considerably lower at the different elution flows. In Table 4 and 5 formulation (I) behaves like (B) in Table 2 because it is just (B) covered with mucoadhesive; formulation (L) is based on (D) and has the same dissolution profile as (D), (E) and (F). Since (D) has a good dissolution it follows that (L) also has a good dissolution. The formulation having (D) as controlled release core has been used for the in vivo trial in Example 5.

In particular, it can be seen that compositions D and L, in Table 5 which were without mucoadhesive coating, were eluted almost completely from the mucous membrane using water flows which were totally inadequate to detach the coated particles.

EXAMPLE 3

Preparation of Dosage Forms for Oral Administration

The mucoadhesive controlled-release granules obtained as described for composition (L) in Example 2, were previously mixed with the extragranular excipients required to inhibit mucoadhesive-coated granule aggregation in the presence of gastrointestinal fluids, in accordance with the percentages shown in Table 6.

TABLE 6

| Ingredients | % |
|---|---|
| MUCOADHESIVE GRANULES (L) | 85 |
| CROSSLINKED POLYVINYLPYRROLIDONE | 10 |
| MAGNESIUM STEARATE | 5 |

No. 1 dull-white hard-gelatine capsules were then filled with this mixture so that every dosage form contained 40 mg of furosemide.

Control of Dosage Forms

The capsules (N) so prepared were subjected to dissolution tests conducted in the conditions described in Example 1. The results obtained are shown in Table 7 and compared with the dissolution profiles obtained with the non-mucoadhesive controlled-release granulate (D) and the mucoadhesive granulate (L) respectively.

TABLE 7

| Time (hours) | % Furosemide Released | | |
|---|---|---|---|
| | D | L | N |
| 1 | 30.9 | 31.0 | 26.1 |
| 2 | 48.4 | 47.9 | 44.6 |
| 4 | 61.4 | 59.9 | 60.5 |
| 8 | 72.5 | 71.3 | 74.9 |
| 12 | >75.0 | >75.0 | >75.0 |
| 24 | >90.0 | >90.0 | >90.0 |

It can be seen that drug release is a function only of the granule characteristics which control release and is not affected by the mucoadhesive coating and by the extragranular excipients contained in the gelatine capsule which carries the composition.

EXAMPLE 4

Long-Term Stability Testing

To determine the consistency in time, of the characteristics of the dosage forms prepared as described in Example 3 were subjected to a stability program at 35° C. (3 months) and at room temperature (3 and 6 months), respectively. Both the assay consistency for the furosemide contained in the capsules expressed as a percent ratio of the initial assay, and the persisting of the formulation release characteristics, were checked by dissolution tests conducted in the conditions described in Example 1. The values obtained, which are shown in Table 8, demonstrate that the formulation characteristics do not change significantly in time.

TABLE 8

| Temp (°C.) | Time (mon.) | Assay % | % Furosemide Released | | | | | |
|---|---|---|---|---|---|---|---|---|
| | | | 1 h | 2 h | 4 h | 8 h | 12 h | 24 h |
| 25 | 0 | 100.0 | 26.1 | 44.6 | 60.5 | 74.0 | >80.0 | >90.0 |
| 25 | 3 | 100.0 | 32.8 | 53.1 | 67.5 | 77.7 | >80.0 | >90.0 |
| 25 | 6 | 99.0 | 32.5 | 53.0 | 68.1 | 77.9 | >80.0 | >90.0 |
| 35 | 3 | 100.0 | 29.9 | 53.1 | 71.1 | 82.8 | >85.0 | >90.0 |

EXAMPLE 5

"In Vivo" Evaluation of Efficacy

This study was conducted in 6 healthy volunteers. Formulation (N) described in Example 3 was evaluated versus a fast-release furosemide formulation (O) obtained from the market: Impugan™. Both formulations contained 40 mg of furosemide.

The study was conducted according to an open-label randomized trial design, which provided for a one-week wash-out between the two treatments. The subjects fasted from 12.00 p.m. of the day preceding treatment. A light breakfast was given 10–15 minutes before treatment, lunch was given 4 hours after administration and dinner was given 9–10 hours after treatment. 200 ml of water with a known salt content were given up to 8 hours from treatment, thereafter no restrictions were set for the intake of liquids. Coffee, tea, alcoholic drinks and heavy physical exercise were not allowed. Urine was collected after 1, 2, 3, 4, 6, 8, 12 and 24 hours from treatment initiation respectively. The results obtained are summarized in FIGS. 1–4.

Figure 2:
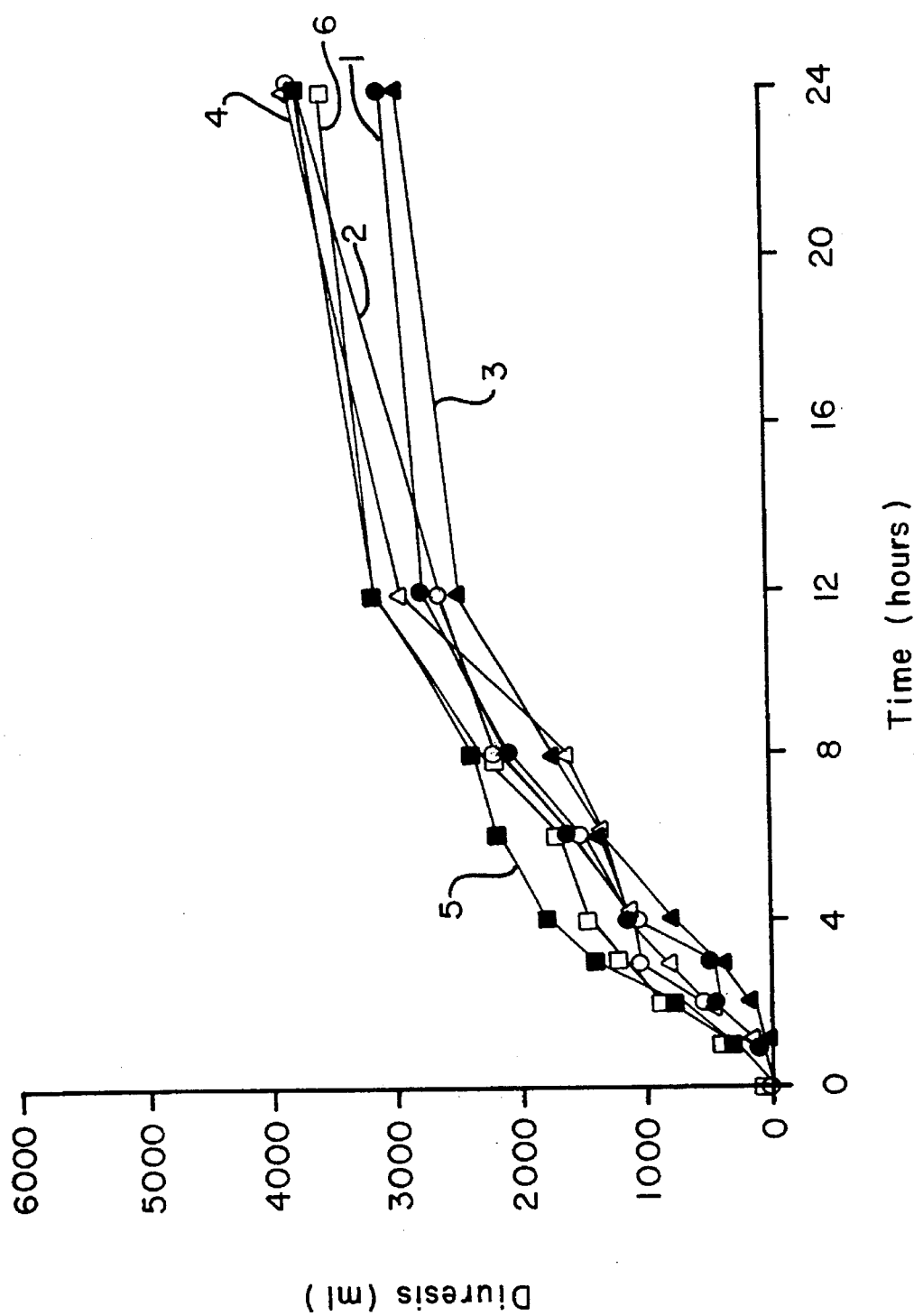
FIG. 2 shows the cumulative diuresis profiles for 6 volunteers after administration of the mucoadhesive controlled-release formulation (N) (present invention).
Figure 3:
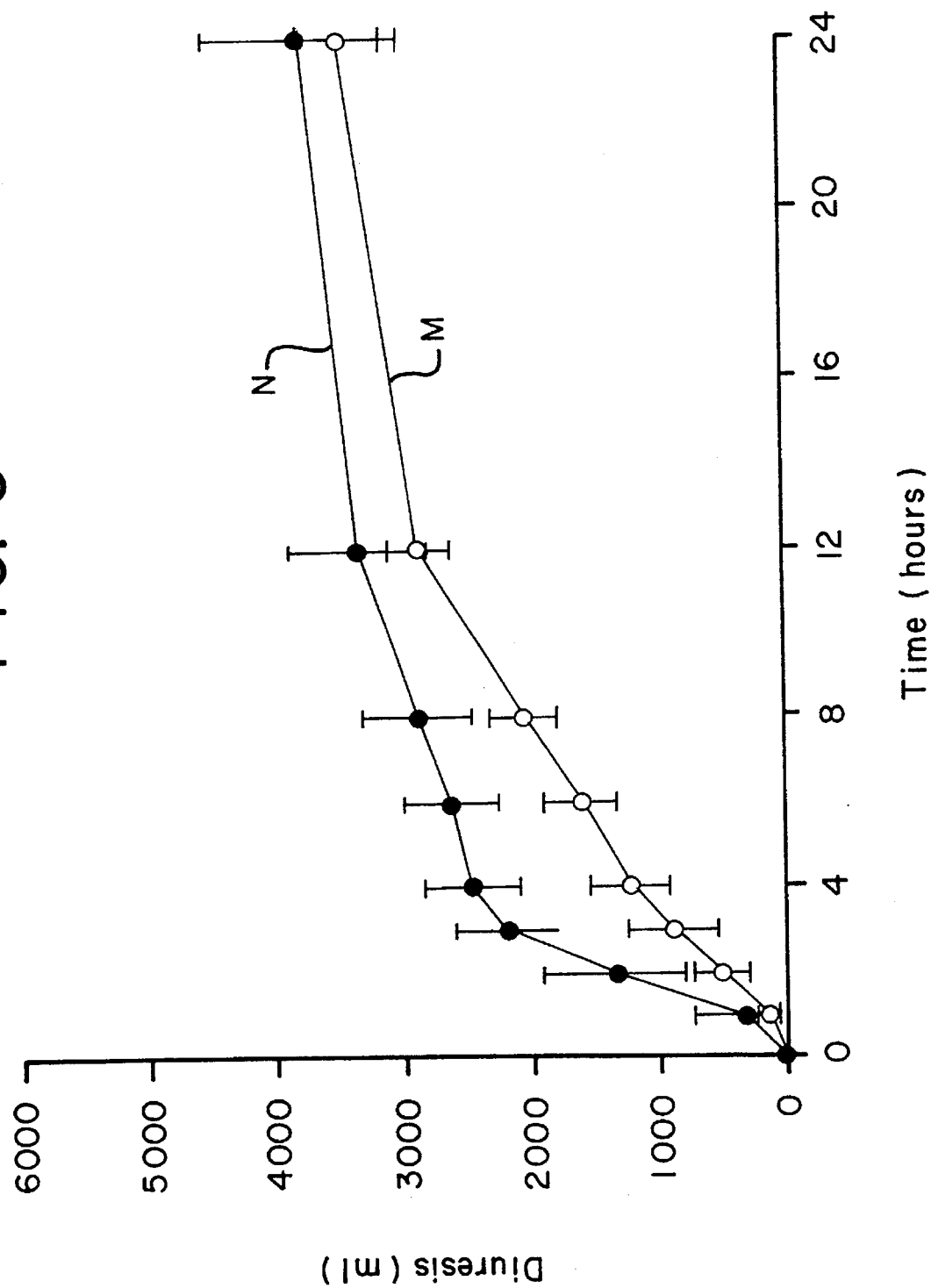
FIG. 3 shows the mean (+/– Standard Deviation) for the cumulative diuresis profiles resulting from the administration of formulations (N) and (O).

The abscissa in all Figures is sampling time expressed as hours. The ordinate in FIGS. 1, 2 and 3 is urine volume in ml, while in FIG. 4 the ordinate is urine flow in ml/hour.

Figure 4:
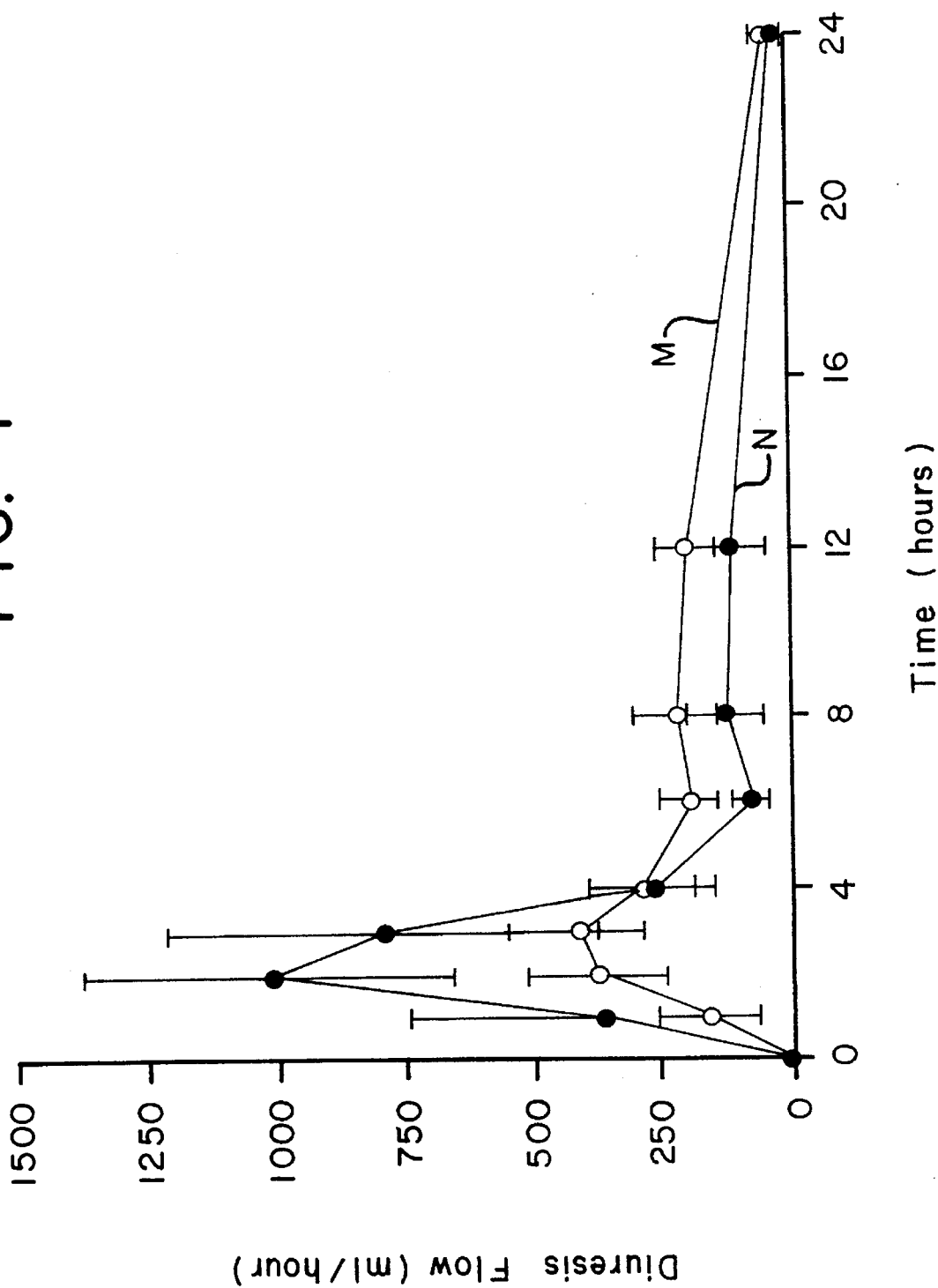
FIG. 4 shows the mean (+/– Standard Deviation) for the urinary flows resulting from the administration of formulations (N) and (O).

As can be seen comparing the diuresis profiles, while the total urine quantity excreted after 24 hours from administration of the fast-release formulation and that excreted following the formulation described in Example 3 are comparable (FIG. 3), the diuresis profiles of the individual patients after administration of the mucoadhesive controlled-release formulation are considerably closer (FIGS. 1 and 2) indicating a substantial reduction in inter-subject variability. Furthermore, in the patients treated with the mucoadhesive formulation, elimination of the diuretic peak is evident, whereas the presence of this peak is evident in the patients treated with the fast-release formulation (FIG. 4).

All documents, patents and patent applications cited herein are incorporated by reference in their entirety. In case of conflicting disclosure, the present disclosure controls.

In light of the above description, it will be apparent to those skilled in the art that the invention is capable of many additions, deletions and modifications within the scope and spirit of the present invention as claimed below.

We claim:

1. An oral dosage form containing an effective amount of furosemide for inducing diuresis in a human and having both control-release and mucoadhesive properties, said dosage form comprising:
   a) a multiplicity of controlled-release microgranules containing said furosemide and one or more granulation excipients having an overall Hydrophilic Lipophilic Balance (HLB) lower than 8; said microgranules having substantially no mucoadhesive properties prior to coating with a mucoadhesive; said granulation excipients being selected from the group consisting of saturated glycerides and polyglycolyzed glycerides;
   b) a coating containing at least one mucoadhesive constituent, said coating having been applied to the surface of said microgranules to substantially completely envelop each microgranule, said coating having been applied in a manner so that it is non-swollen by water, the coating enveloping each microgranule being substantially detached from coatings enveloping other microgranules, and said coating ensuring adhesion of the coated microgranules to the mucous membrane of the gastrointestinal tract; and
   c) extragranular excipients mixed with the mucoadhesive microgranules, facilitating non-aggregation and dispersion of the mucoadhesive microgranules over the mucous membrane of the gastrointestinal tract and detachment of the coating enveloping each microgranule from the coatings enveloping other microgranules.

2. A pharmaceutical composition according to claim 1, wherein the granulation excipients comprise hydrogenated castor-oil and mixtures of polyglycolyzed and polyoxyethylenated glycerides.

3. A composition according to claim 1, wherein the mucoadhesive polymer or polymers are chosen from a group consisting of carbomer, polycarbophil, hydroxypropylmethylcellulose, hydroxypropylcellulose and mixtures of at least two of the foregoing.

4. A composition according to claim 1, wherein the mucoadhesive coating comprises at least one mucoadhesive constituent and at least one non-mucoadhesive constituent, and the weight ratio between the at least one mucoadhesive constituent and the at least one non-mucoadhesive constituent is within the range from 20:1 to 0.2:1.

5. A composition according to claim 1, wherein the mucoadhesive coating comprises at least one mucoadhesive constituent and at least one non-mucoadhesive constituents, the weight ratio between the at least one mucoadhesive constituent and the at least one non-mucoadhesive constituent is within the range from 5:1 to 0.5:1.

6. A composition according to claim 1, wherein the weight ratio between the controlled-release units and the at least one mucoadhesive constituent of said coating is within the range between 5:1 and 0.1:1.

7. A composition according to claim 1, wherein the weight ratio between the controlled-release units and the at least one mucoadhesive constituent of said coating is within the range between 2.5:1 and 0.25:1.

8. A composition according to claim 1, wherein the mean geometric diameter of the microgranules coated with the mucoadhesive coating does not exceed 600 microns.

9. A composition according to claim 1 wherein the extragranular excipients comprise at least one hydrophobic substance delaying hydration of the mucoadhesive coating and at least one disintegrating substance promoting dispersion of the coated microgranules over the mucous membrane of the gastrointestinal tract.

10. A composition according to claim 9, wherein the hydrophobic substance is chosen from the group consisting of magnesium stearate, calcium stearate, talc, and combinations of at least two of the foregoing.

11. A composition according to claim 9, wherein the disintegrating substance is chosen from the group consisting of crosslinked polyvinylpyrrolidone, carboxymethyl starch, croscarmellose sodium, starch, and combinations of at least two of the foregoing.

12. A composition according to claim 7, wherein based on the total ingredients contained in the dosage form, the percentage by weight of the hydrophobic ingredient is within the range between 1 and 10% and that of the disintegrating ingredient is within the range between 2 and 20%.

13. A dosage form according to claim 1, wherein elements (a), (b) and (c) are contained in a hard gelatine capsule.

14. A process for preparing a pharmaceutical composition according to any one of claims 1–13, comprising the steps of:
   a) granulating the active ingredient with one or more granulating excipients having an overall HLB lower than 8 to obtain controlled-release microgranules;
   b) mixing the controlled-release microgranules with a material comprising at least one mucoadhesive constituent;

c) dry granulating said mixture;

d) crumbling said dry granulate; and e) selecting granules of a desired size.

15. The process of claim 14, said mixing step taking place in the presence of a lubricant.

16. A method for increasing diuresis in a human subject in need of such treatment comprising administering to said subject an oral dosage form according to any one of claims 1–13.

17. A composition according to claim 1 wherein the granulation excipients comprise one or more polyethylene glycol monoesters or diesters of one or more fatty acids.

18. A composition according to claim 1 wherein the granulation excipients comprise products of alcoholysis of hydrogenated vegetable oils.

19. A composition according to claim I wherein the granulation excipients comprise products of esterification of saturated fatty acids.

20. A composition according to claim 1 wherein the granulation excipient comprises one or more glycerol monoesters, diesters, or triesters of fatty acids.

21. A composition according to claim 17 wherein said fatty acids are selected from the group consisting of caprylic acid, capric acid, lauric acid, myristic acid, palmitic acid, and stearic acid.

22. A composition according to claim 20 wherein said fatty acids are selected from the group consisting of caprylic acid, capric acid, lauric acid, myristic acid, palmitic acid, and stearic acid.

23. A composition according to claim 1 wherein said granulation excipient comprises glyceryl monostearate.

24. A composition according to claim 1 wherein said granulation excipient comprises glyceryl monopalmitate stearate.

25. A composition according to claim 1 wherein said granulation excipient comprises glyceryl monomyristate.

26. A composition according to claim 1 wherein said granulation excipient comprises polyethyleneglycol monostearate.

27. A composition according to claim 1 wherein said granulation excipient comprises polyethyleneglycol palmitate stearate.

* * * * *

UNITED STATES PATENT AND TRADEMARK OFFICE
CERTIFICATE OF CORRECTION

PATENT NO. : 5,571,533
DATED : Nov. 5, 1996
INVENTOR(S) : Giancarlo SANTUS, Giuseppe BOTTONI, Caterina LAZZARINI It is certified that error appears in the above-indentified patent and that said Letters Patent is hereby corrected as shown below:

Title page, [30] Foreign Application Priority Data:
   Change "MI93A1049" to --MI93A001049--.

Signed and Sealed this

Eleventh Day of March, 1997

Attest:

BRUCE LEHMAN

Attesting Officer    Commissioner of Patents and Trademarks